United States Patent
Witham et al.

(10) Patent No.: US 7,421,851 B2
(45) Date of Patent: **\*Sep. 9, 2008**

(54) APPLIANCE FOR DISINFECTION OF HVAC SYSTEMS

(75) Inventors: David L. Witham, Valencia, CA (US); Thomas M. Veloz, Valencia, CA (US); Thomas C. Bowles, Huntington Beach, CA (US); Roberto Arance, Castaic, CA (US); Keith Crawford, Canyon Country, CA (US); Jon W. Orr, Thousand Oaks, CA (US); Richard N. Metzger, Pasadena, CA (US); Larry F. Randall, Santa Clarita, CA (US)

(73) Assignee: UltraViolet Devices, Inc., Valencia, CA (US)

( * ) Notice: Subject to any disclaimer, the term of this patent is extended or adjusted under 35 U.S.C. 154(b) by 128 days.

This patent is subject to a terminal disclaimer.

(21) Appl. No.: 11/485,933

(22) Filed: Jul. 12, 2006

(65) Prior Publication Data

US 2006/0254298 A1 Nov. 16, 2006

Related U.S. Application Data

(63) Continuation of application No. 10/048,904, filed as application No. PCT/US00/25319 on Sep. 15, 2000, now Pat. No. 7,107,778.

(51) Int. Cl.
*F25D 23/00* (2006.01)
*A62B 7/08* (2006.01)
*B01L 1/04* (2006.01)

(52) U.S. Cl. .......................... 62/264; 422/121; 454/187

(58) Field of Classification Search ................... 62/264; 422/121; 454/187
See application file for complete search history.

(56) References Cited

U.S. PATENT DOCUMENTS

| | | | |
|---|---|---|---|
| 3,877,152 A | 4/1975 | Gorman | |
| 5,106,512 A | 4/1992 | Reidy | |
| 5,458,186 A | 10/1995 | Lee et al. | |
| 5,523,057 A | 6/1996 | Mazzilli | |
| 5,601,786 A | 2/1997 | Monagan | |
| 5,616,172 A * | 4/1997 | Tuckerman et al. | 96/16 |
| 5,664,340 A | 9/1997 | Brown | |
| 5,742,063 A | 4/1998 | Scroggins et al. | |
| 5,833,740 A | 11/1998 | Brais | |
| 5,837,207 A | 11/1998 | Summers | |
| 5,891,399 A | 4/1999 | Owesen | |
| 5,894,130 A * | 4/1999 | Bach | 250/436 |
| 5,902,552 A * | 5/1999 | Brickley | 422/121 |
| 5,968,455 A * | 10/1999 | Brickley | 422/121 |
| 6,746,134 B1 | 6/2004 | Guzorek | |
| 6,809,326 B2 | 10/2004 | Disabito et al. | |
| 7,107,778 B1 * | 9/2006 | Witham et al. | 62/264 |

FOREIGN PATENT DOCUMENTS

WO    WO 01/30399    5/2001

\* cited by examiner

*Primary Examiner*—William C Doerrler
(74) *Attorney, Agent, or Firm*—Cislo & Thomas, LLP (57) ABSTRACT

An application and method for disinfecting HVAC systems that includes features for protecting service personnel from unintended exposure to ultraviolet radiation. The safeguards include an interlock that prevents illumination of germicidal lamps when their enclosure case is not properly attached to a duct.

17 Claims, 6 Drawing Sheets

APPLIANCE FOR DISINFECTION OF HVAC SYSTEMS

CROSS-REFERENCE TO RELATED APPLICATION(S)

This document is a continuation application which is related to, and claims priority from, U.S. patent application Ser. No. 10/048,904, filed Feb. 4, 2002 now U.S. Pat. No. 7,107,778, entitled "Appliance For Disinfection of HVAC Systems," incorporated herein by this reference thereto, which is, in turn, related to, and claims priority from, PCT Patent Application Number PCT/US00/25319, filed Sep. 15, 2000, also entitled "Appliance For Disinfection of HVAC Systems," also incorporated herein by reference thereto.

TECHNICAL FIELD

The present invention relates to an appliance for use in the disinfection of heating ventilation and air conditioning systems ("HVAC"). More particularly, the present invention relates to a device for killing microorganisms in both an air stream and/or stationary components within an HVAC system such as cooling coils, duct components, and filter media, by irradiation with ultraviolet ("UV") light.

Prior art appliances were designed to retain germicidal lamps in a variety of inefficient and costly designs. Some lamps were affixed to a base with a synthetic potting material. Others have used an awkward retaining device that may not prevent the installation of incorrect lamps. Other solutions provide a means to mount the germicidal lamp within the device, but are costly or difficult to manufacture.

BACKGROUND ART

Ultraviolet light having a wavelength in a range from 180 to 300 nm has been used for the disinfection of air, water, and surfaces for many years. Wavelengths near 253.7 nm are particularly useful for killing bacteria, viruses, fungus, mold, and spores, and are conveniently generated by low pressure mercury vapor lamp. Many devices and methods for utilizing UV for disinfection include devices for use in HVAC equipment for treatment of air streams and surfaces. However, these related art devices have not adequately addressed safety and performance issues.

"Disinfection" refers to killing pathogenic or otherwise undesirable micro-organisms. Products using short-wave ultraviolet radiation with wavelengths in the range of 180 to 350 nm have been used to disinfect air streams in residential and commercial HVAC systems. This is a high energy form of radiation that is not visible to humans. While this high energy ultraviolet light is capable of destroying a variety of biological pathogens and non-pathogenic, but nevertheless undesirable organisms, it is also hazardous to humans. Short wavelength ultraviolet radiation has been determined to be the cause of skin cancers, such as melanoma, and some cases of non-Hodgkin's lymphoma by the National Center for Chronic Disease Prevention at the Centers for Disease Control and Prevention and by the National Cancer Institute. The eyes are particularly susceptible to damage caused by ultraviolet radiation. The upper threshold for exposure of the human eye to ultraviolet light has been set at 3 millijoules per square centimeter.

The lamps typically used to produce ultraviolet radiation for germicidal application produce a flux of ultraviolet radiation, well in excess of this threshold and, often 100 to 1000 times higher than this threshold. Therefore, protective measures should be taken to protect workers and consumers who use ultraviolet light for germicidal applications.

Protective eyewear can adequately protect workers from health risk while working with ultraviolet devices. However, examination of Worker's Compensation Insurance claims reveal that one-half of the ultraviolet radiation related eye injuries occurred to workers who were in possession of, but neglected to use, proper protective eyewear.

In the past, sterilization and disinfection units were inadequately protected. While some units have electrical or mechanical mechanisms that may shut off a UV emitting germicidal lamp when it is removed from its enclosure, the device may be energized prior to installation, thereby subjecting the user or service person installing the unit to ultraviolet radiation.

DISCLOSURE OF THE INVENTION

The present invention provides an integrated appliance for disinfection of HVAC systems that overcomes the deficiencies of prior art devices by providing a separate lamp assembly for each germicidal lamp. The invention may further provide that each lamp assembly can be separately removed from the appliance, and may further provide an optical signal for assessing performance of the lamp mounted in the lamp assembly. The invention may further provide novel switch assemblies that prevent application of electrical power when an enclosure containing the lamps is open for servicing, thus preventing exposure of service personnel to ultraviolet radiation.

The basic components of the system are an enclosure, removable UV lamp assemblies, a power supply to supply electrical power to the lamps, and various mechanical and electrical features to improve performance, convenience and safety. The present invention reduces the risk that those involved in installation and maintenance of HVAC equipment will be exposed to ultraviolet radiation when the lamps are serviced when the lamps are replaced, or when the unit is not properly positioned in a duct. The present invention may also provide an indication of lamp operation visible from the outside of the duct to eliminate any need for direct visual observation of the lamps. An additional safety feature shuts off power to the lamps that produce ultraviolet radiation whenever a service person attempts to open the enclosure or remove the lamps to prevent exposure to harmful UV radiation. Other features of the invention provide improved performance and also ease of maintenance.

The present appliance is located within a self-contained unit that is installed in a portion of the duct work of an HVAC system or within a central HVAC appliance, such as a furnace, air conditioner, or ventilating unit. The unit is generally mounted through an opening in the side of an HVAC duct. The electrical connections and ports are located on the outside of the duct, while the mercury vapor lamps that produce UV are located within the duct. The present appliance for disinfection comprises lamps that are optimized for an HVAC system and that can be mounted in the system. The present appliance for disinfection of HVAC systems is designed to allow assessment of germicidal lamp performance without the risk of exposure to ultraviolet radiation.

BRIEF DESCRIPTION OF THE DRAWING

For better understanding of the present invention, reference is made to the below-referenced accompanying Drawing. Reference numbers refer to the same or equivalent parts of the present invention throughout the several figures of the Drawing.

MODE(S) FOR CARRYING OUT THE INVENTION

Figure 1A:
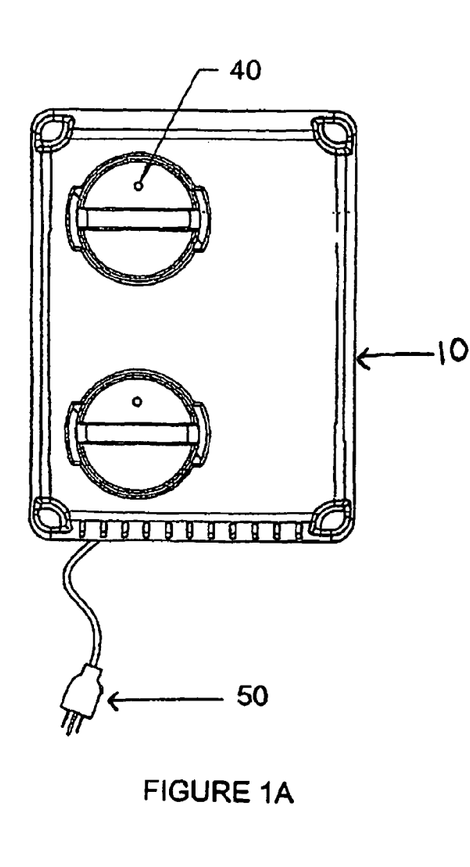
FIG. 1A is a front view of an appliance for disinfecting an HVAC system, in accordance with the present invention.
Figure 1B:
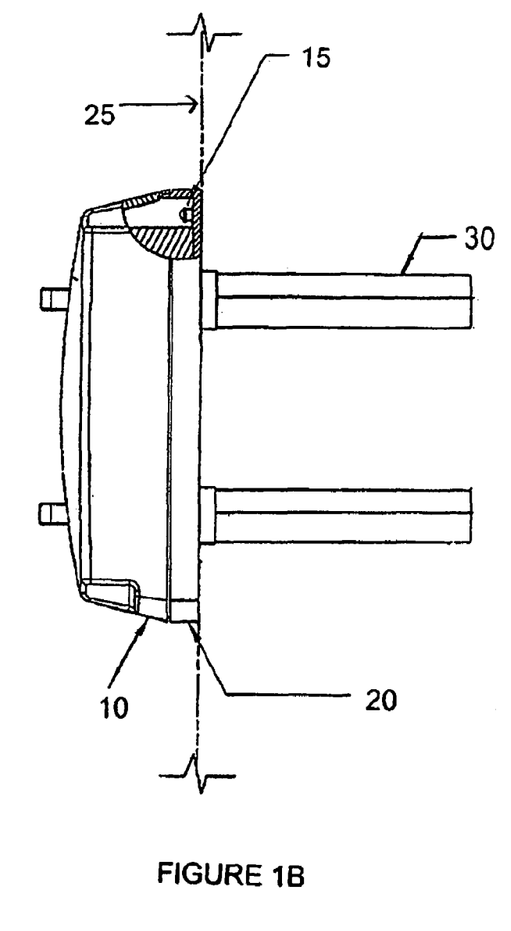
FIG. 1B is a side view of the appliance, as shown in FIG. 1A.

As shown in FIGS. 1A and 1B, in one embodiment, the appliance comprises an enclosure case 10 and a base 20. Base 20 is mounted to a wall of an HVAC duct 25. One or more openings are cut in the wall 25 of the duct for the germicidal lamps 30 to project into the interior of the duct Base 20 includes a mechanical mount for one or more germicidal lamps, the electrical connections to the lamps, and a power supply and ballast combination (not shown). The number of germicidal lamps 30 is determined by the intensity of the ultraviolet radiation required for the particular application. The germicidal lamps 30 may be of a commercial design or specially made for this application. To insure the best match between lamp characteristics and the electrical properties of the power supply and ballast combination, in preferred embodiments, germicidal lamps 30 are provided with specially designed mounts to engage lamp mounts on base 20 as described below in greater detail. The germicidal lamps 30 may be configured as a single longitudinal tube (single or double ended) or a multi-axial tube.

Figure 2:
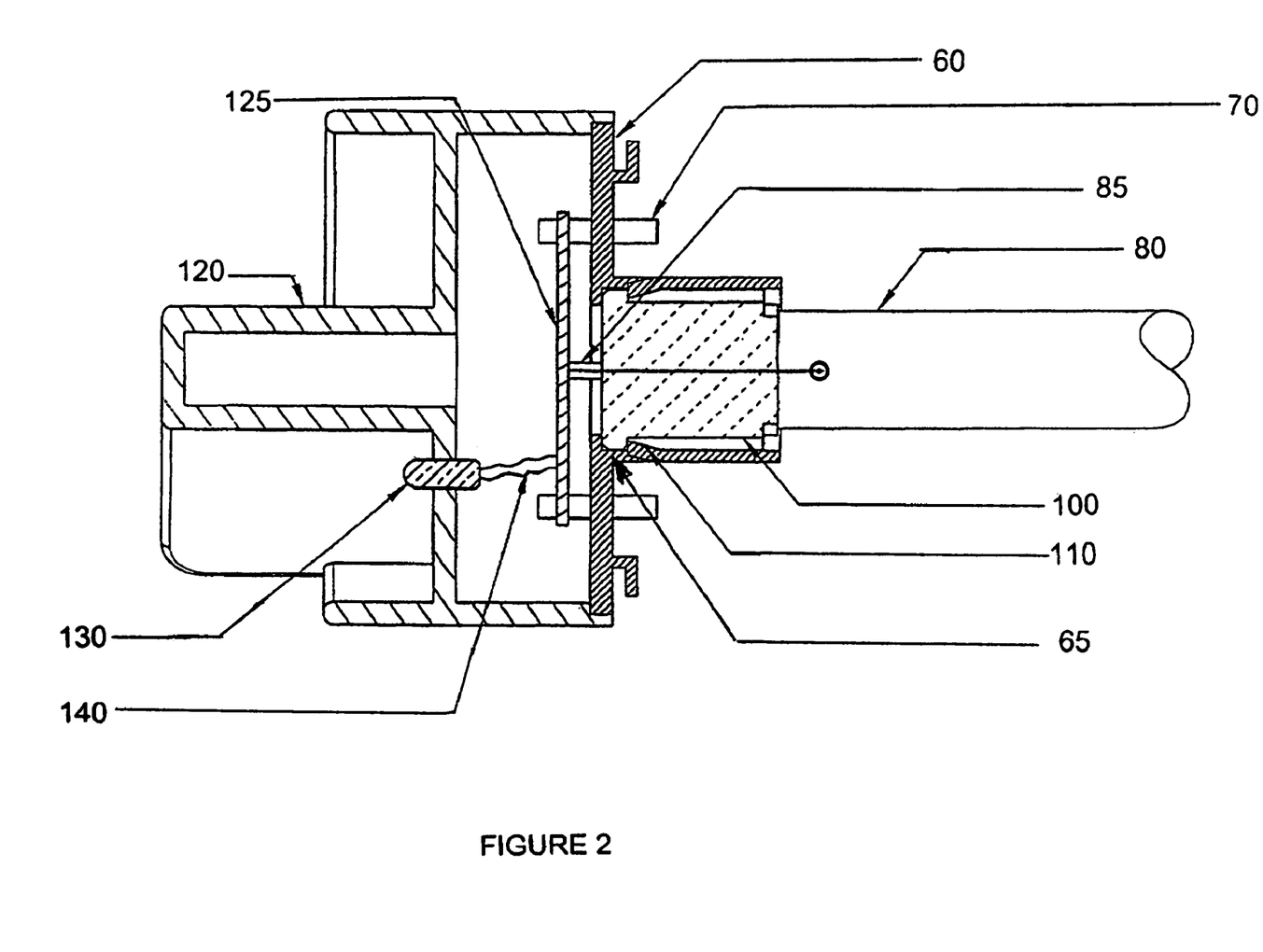
FIG. 2 is a cross-sectional view of a lamp assembly in the appliance, as shown in FIGS. 1A and 1B.

The germicidal lamps 30 are mounted in a specially designed socket described below in greater detail. As shown in FIG. 2, each lamp socket includes electrical connections to the lamp 80 therein mounted. As also shown in FIG. 2, in preferred embodiments, the lamp socket 65 is formed integrally with handle base 60 to form lamp assembly 75 which is installed with the enclosure case 10. A section view of the lamp assembly 75 is also shown in FIG. 2.

Figure 3:
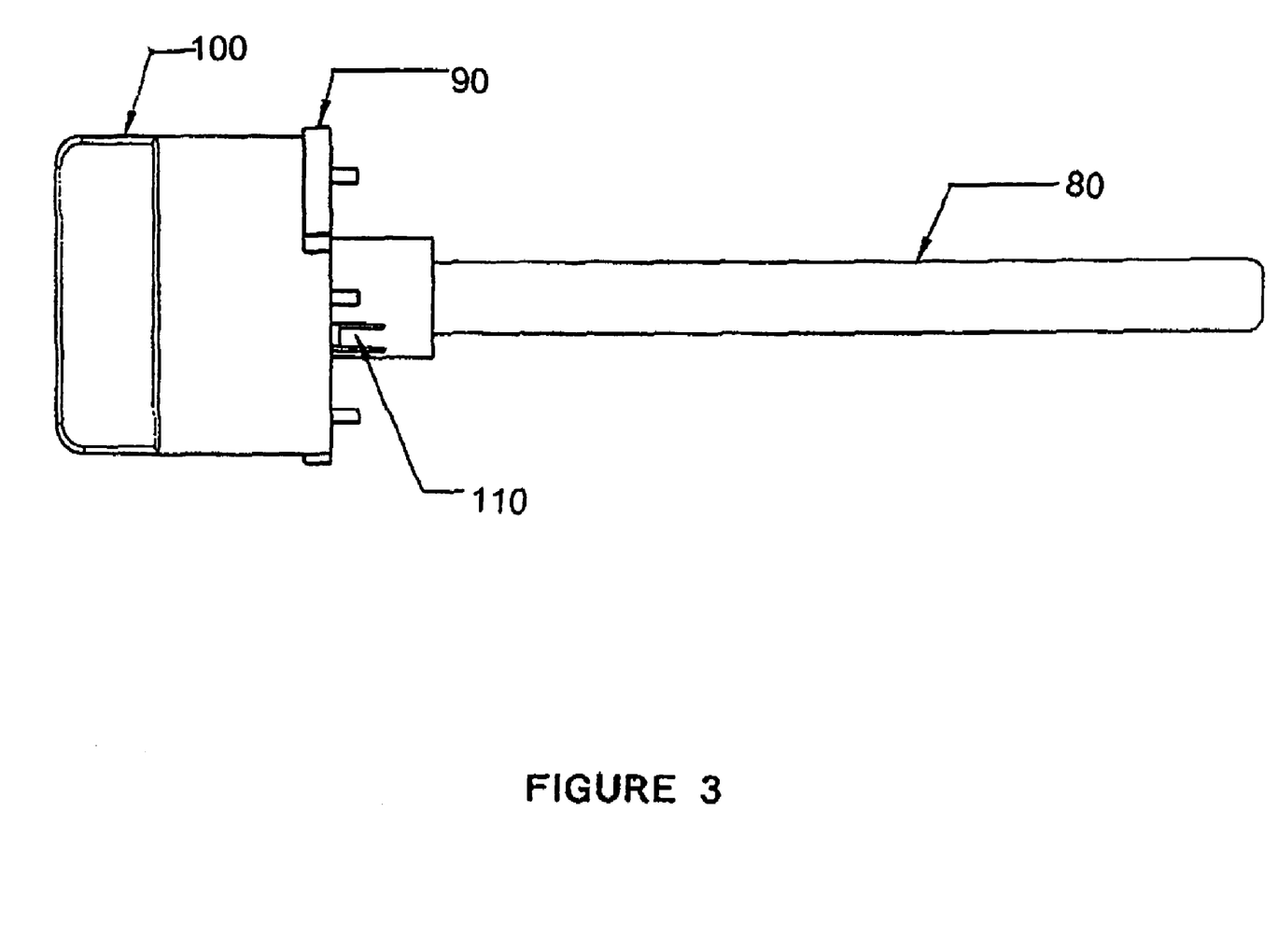
FIG. 3 is a side view of the lamp assembly, as shown in FIG. 2.

Each lamp 80 is mounted separately in its own lamp assembly 75, allowing each lamp to be separately removed from service. As shown in FIG. 3 and in more detail in FIG. 5, the lamp assembly 75 includes a handle base 60, a handle cover 120, a connection circuit board 125, and an indicator light 130 of a lamp indicator 40 which, as discussed below in greater detail, provides an optical signal indicative of the state of operation of the lamp 80 mounted on the particular lamp assembly 75 (FIG. 2). Lamp assembly 75 is attached to the enclosure case 10 using a bayonet mount (not shown). A handle 100 attached to the lamp assembly 75 is grasped and rotated to release the lamp assembly 75 from the enclosure case 10 when it is necessary to service or replace the lamp 80. An end view of the enclosure case 10, with two lamp assembles 75 is shown in FIG. 1A.

The invention further includes a duct mounting interlock 15 that prevents electrical power from reaching the ultraviolet lamps 80 unless the enclosure case 10 is installed on an HVAC duct (FIG. 1B). Electrical power for the germicidal lamps 80 is routed through a switch that is closed when a unit is attached to a duct or appliance. In preferred embodiments, the switch 230 is a paddle switch mounted in an appliance. When switch 230 is closed by attaching the appliance to an HVAC duct, electrical current can reach the germicidal lamps 80.

In embodiments with provision for more than one lamp assembly 75 in an enclosure case 10, power will not be supplied to any lamp assemblies 75 unless all lamp assemblies 75 are installed. This aspect of the invention protects service personnel from exposure to UV radiation that would otherwise escape from the enclosure case 10 through unused openings for lamp assemblies 75. The presence of lamp assemblies 75 may be detected by, for example, mechanical switches located adjacent to bayonet mounts for the lamp assemblies 75.

Figure 4A:
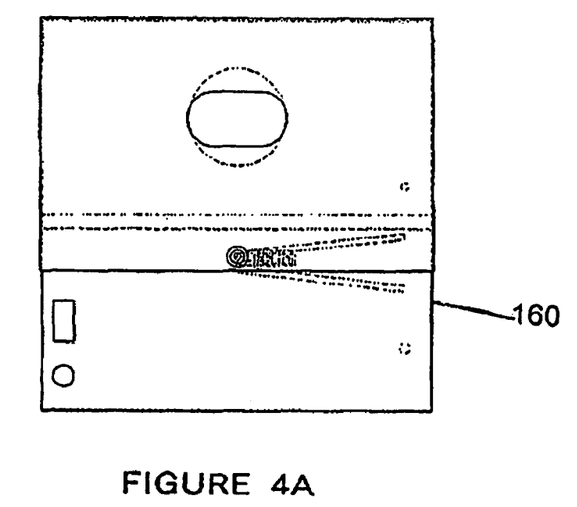
FIG. 4A is a front view of an appliance for disinfecting an HVAC system, in accordance with an alternative embodiment of the present invention.
Figure 4B:
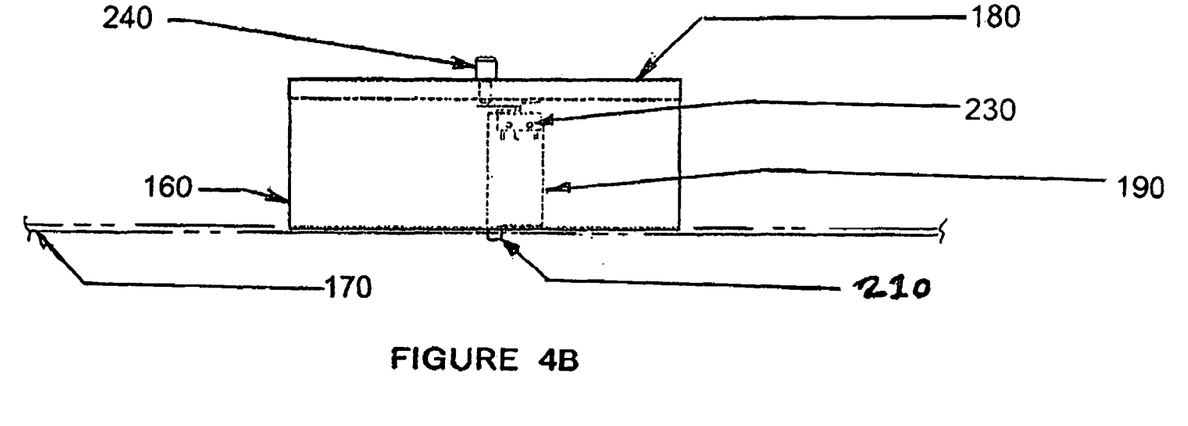
FIG. 4B is a cross-sectional view of the appliance, as shown in FIG. 4A.
Figure 5:
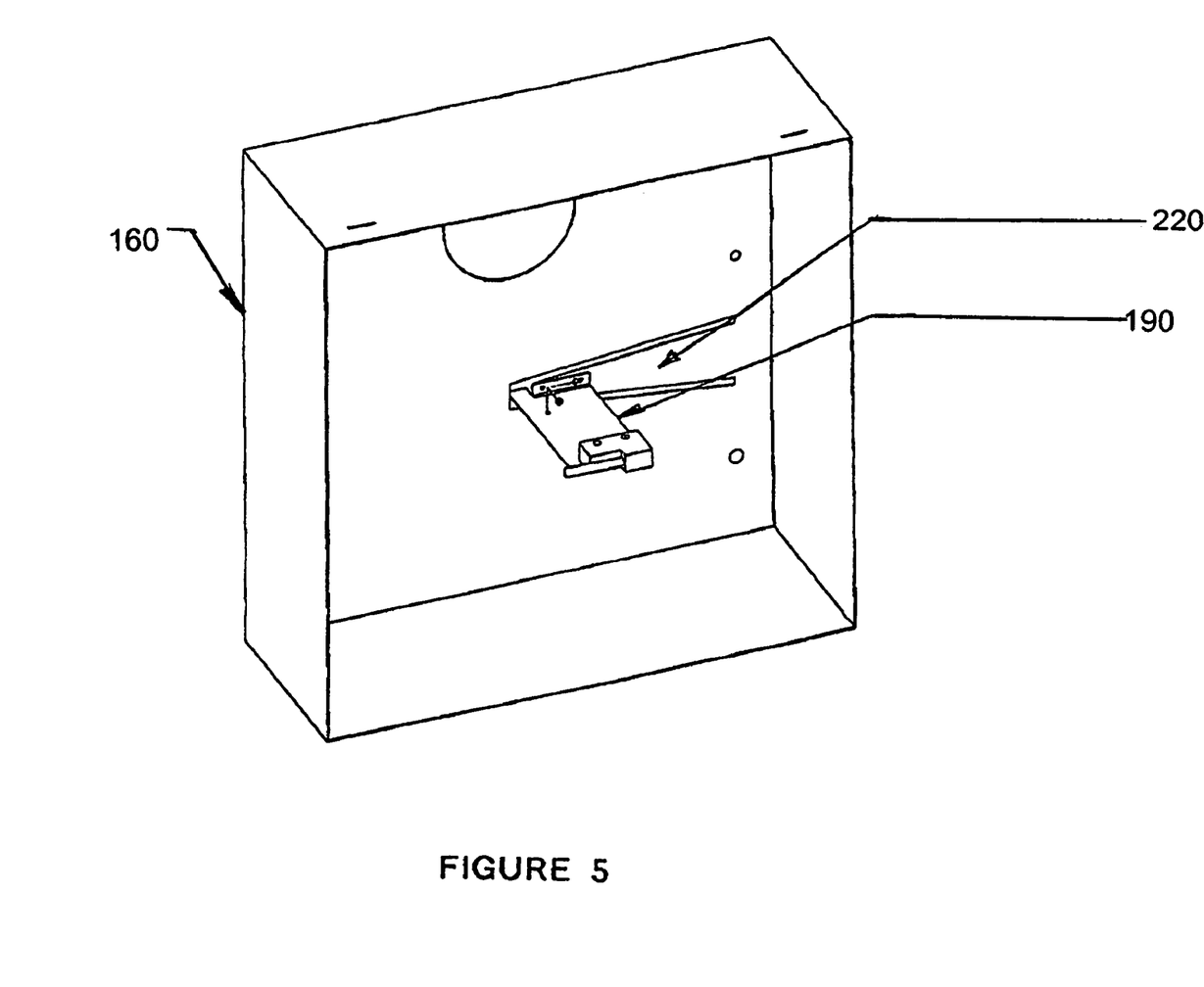
FIG. 5 is a rear perspective view of the appliance, as shown in FIG. 4A.

Another embodiment of the appliance that prevents power from reaching the germicidal lamps 80 unless the enclosure case 10 is installed in an HVAC duct is depicted in FIGS. 4A, 4B, and 5. A side sectional view of this embodiment is shown in FIG. 4B. In this embodiment, mounts for UV lamps 80 are installed in a narrow box-shaped housing 160. In this embodiment, two conditions must be met before power is applied to the germicidal lamps 80. First, housing 160 must be mounted on the wall 170 of a duct. Second, cover 180 must be attached to housing 160. Under these conditions, UV light will not be emitted unless the appliance of the present invention is attached to an HVAC duct, on one side, and that the cover 180 is attached to the opposite side. Thus, UV light should not be able to escape from the appliance.

Switch bracket 190 is mounted on a portion of the wall of housing 160 that is made flexible by cutouts made in wall forming a "v" shaped leaf spring 220. When housing 160 (FIG. 4) is mounted on duct wall 170, bracket tab 190 is deflected inward against spring pressure produced by leaf spring 220. As a consequence, switch bracket 190, which is attached to bracket tab 210 moves inward as well.

Interlock switch 230 is fixed to the end of switch bracket 190 opposite the point at which switch bracket 190 is attached to leaf spring 220. Thus, when switch bracket 190 is deflected inward, interlock switch 230 is carried forward as well. When interlock switch 230 contacts cover screw 240, which is used to secure cover 180 in place, interlock switch 230 is deflected backward, thus closing an electrical circuit that supplies power to germicidal lamps 80 within the appliance. Thus, unless the appliance is mounted on an HVAC duct, pressing bracket tab 210 inward, and cover 180 is attached to housing 160, power will not be applied to the germicidal lamps 80, and no UV radiation will be produced. This mechanism will help to prevent inadvertent exposure to UV radiation produced by those who service and maintain the appliance.

Figure 6:
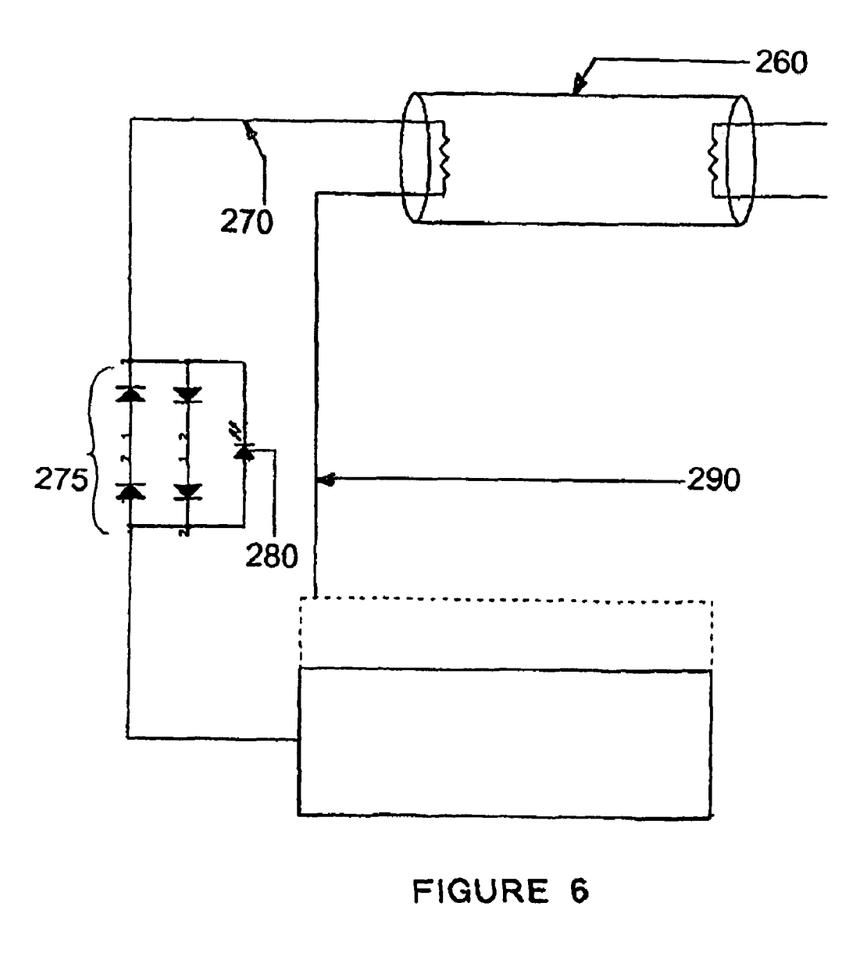
FIG. 6 is a schematic diagram of the circuitry in an appliance for disinfecting an HVAC system, in accordance with the present invention.

An additional safety feature of the invention is a visible indicator as to whether each lamp 80 installed in a appliance according to the invention is illuminated. As shown in FIG. 6, AC power is supplied to the filaments of a low pressure mercury vapor germicidal lamp 260 through a pair of power circuits 270. Two pair of oppositely oriented diodes 275 are interposed in an arm of one power circuit 270. A light emitting diode ("LED") 280 illuminates when a voltage drop is present across the diode pair. The LED 280 is only illuminated for a half cycle of the power wave form, but at frequencies of approximately 60 Hz used in most installations, the off time is not detectable. Lamp failure is therefore readily detected, as the LED 280 is not illuminated when there is no current flowing through the diodes 275.

The lamp base 20 of the present invention is specifically implemented to prevent the installation of germicidal lamps 80 not intended for use with the present invention. Although there are many sources for germicidal lamps 80, it is preferable to use lamps 80 optimized for use with the inventive appliance disclosed and claimed herein. In some cases, lamps 80 not designed for use with the present invention may not deliver the energy required by the particular installation.

As shown in FIG. 2, the present invention employs a lamp base 20 that engages protrusions formed on the lamp base 20 with one-way barbs 110. This engagement mechanism securely fastens the germicidal lamp 80 to the lamp base 20.

Information as herein shown and described in detail is fully capable of attaining the above-described object of the invention, the presently preferred embodiment of the invention, and is, thus, representative of the subject matter which is broadly contemplated by the present invention. The scope of the present invention fully encompasses other embodiments which may become obvious to those skilled in the art, and is to be limited, accordingly, by nothing other than the appended claims, wherein reference to an element in the singular is not intended to mean "one and only one" unless explicitly so stated, but rather "one or more." All structural and functional equivalents to the elements of the above-described preferred embodiment and additional embodiments that are known to those of ordinary skill in the art are hereby expressly incorporated by reference and are intended to be encompassed by the present claims.

Moreover, no requirement exists for a device or method to address each and every problem sought to be resolved by the present invention, for such to be encompassed by the present claims. Furthermore, no element, component, or method step in the present disclosure is intended to be dedicated to the public regardless of whether the element, component, or method step is explicitly recited in the claims. However, that various changes and modifications in form, material, and fabrication material detail may be made, without departing from the spirit and scope of the inventions as set forth in the appended claims, should be readily apparent to those of ordinary skill in the art. No claim herein is to be construed under the provisions of 35 U.S.C. § 112, sixth paragraph, unless the element is expressly recited using the phrase "means for."

What is claimed is:

1. A disinfecting appliance for disinfecting an HVAC system, comprising:
    at least one germicidal lamp located in an enclosure being mountable on at least one element selected from a group consisting of an HVAC duct and an HVAC appliance;
    a source of electrical power for the germicidal lamp; and
    a switch that turns off power to the at least one germicidal lamp, the switch comprising a duct mounting interlock that prevents the electrical power source from reaching the at least one germicidal lamp unless the enclosure is also mounted on the at least one element selected from the group consisting of the HVAC duct and the HVAC appliance.

2. The appliance of claim 1, further comprising:
    a base;
    a power circuitry located within the base; and
    a lamp assembly mounted in the base.

3. The appliance of claim 2, wherein the lamp assembly comprises:
    a handle base;
    a handle cover; and
    a connection circuit board through which power is provided to at least one germicidal lamp by way of a connector pin.

4. The appliance of claim 2, wherein the lamp assembly is mounted in the base using a bayonet mount.

5. The appliance of claim 2, further comprising an electrically powered indicator of lamp illumination.

6. The appliance of claim 5, wherein the electrically powered indicator of lamp illumination comprises:
    at least two pair of oppositely directed diodes; and
    a light emitting diode wired in parallel to thereto.

7. A disinfecting appliance for an HVAC system, comprising:
    at least one germicidal lamp located in an enclosure being mountable on at least one element selected from a group consisting of an HVAC duct and an HVAC appliance;
    a source of electrical power for the germicidal lamp;
    a switch that turns off power to the at least one germicidal lamp, the switch comprising a duct mounting interlock that prevents the electrical power source from reaching the at least one germicidal lamp unless the enclosure is also mounted on the at least one element selected from the group consisting of the HVAC duct and the HVAC appliance; and
    a lamp transparent lamp base that allows monitoring of germicidal lamp illumination.

8. The appliance of claim 7, wherein the interlock is a mechanical switch interposed in a circuit that supplies electrical power to at least one germicidal lamp that is in a conducting condition when the enclosure is mounted on an HVAC duct or appliance, and in a non-conducting condition when the enclosure is not mounted on an HVAC duct or appliance.

9. An appliance for disinfecting an HVAC system comprising:
    at least one germicidal lamp in attached to a lamp assembly, the lamp assembly being removably mounted on an enclosure, the enclosure being mounted on at least one element selected from a group consisting essentially of an HVAC duct and an HVAC appliance; and
    a switch positioned close to the lamp assembly, and interposed in a circuit carrying power to the at least one germicidal lamp, the switch being in an open position when the lamp assembly is removed from the enclosure, and closed when the lamp assembly is present, the switch comprising an interlock switch that prevents the electrical power source from reaching the at least one germicidal lamp unless the enclosure is also mounted on the at least one element selected from the group consisting of the HVAC duct and the HVAC appliance, the interlock switch comprising a paddle switch.

10. An apparatus for monitoring the operation of at least one germicidal lamp used for disinfecting an HVAC system, the at least one germicidal lamp located in an enclosure that is mounted on at least one element selected from a group consisting of an HVAC duct and an HVAC appliance, the apparatus comprising a monitoring circuit, the circuit comprising:
    two pairs of oppositely directed diodes connected in parallel; and
    a light emitting diode connected in parallel therewith, the monitoring circuit being wired in series with a power circuit supplying power to the at least one germicidal lamp.

11. A lamp assembly comprising:
    a germicidal lamp located in an enclosure that is mounted on at least one element selected from a group consisting of an HVAC duct and an HVAC appliance;
    a lamp base;
    a handle with which the lamp assembly can be manually manipulated;
    a power circuit;
    a connection circuit board; and a switch that turns off power to the germicidal lamp, the switch comprising a duct mounting interlock that prevents the electrical power source from reaching the germicidal lamp unless the enclosure is also mounted on the at least one element selected from the group consisting of the HVAC duct and the HVAC appliance, wherein the germicidal lamp is permanently attached to a socket, the socket being removably mounted in a lamp assembly.

12. The lamp assembly of claim 11, further comprising an optical signal indicative of the state of operation of the germicidal lamp of the lamp assembly.

13. The lamp assembly of claim 12, wherein the optical signal is provided by a light pipe.

14. The lamp assembly of claim 12, wherein the optical signal is provided by an electrically powered lamp.

15. An appliance for disinfection of HVAC systems comprising a plurality of lamp assemblies located in an enclosure that is mounted on at least one element selected from a group consisting of an HVAC duct and an HVAC appliance, wherein each lamp assembly is separately provided with electrical power, each lamp assembly of the plurality of lamp assemblies comprising:

a germicidal lamp;

a lamp base;

a handle with which the lamp assembly can be manually manipulated;

a power circuit;

a connection circuit board; and a switch that turns off power to the germicidal lamp, the switch comprising a duct mounting interlock that prevents the electrical power source from reaching the germicidal lamp unless the enclosure is also mounted on the at least one element selected from the group consisting of the HVAC duct and the HVAC appliance, wherein the germicidal lamp is permanently attached to a socket, the socket being removably mounted in a lamp assembly.

16. A disinfecting appliance for an HVAC system comprising:

at least one germicidal lamp located in an enclosure that is mounted on at least one element selected from a group consisting of an HVAC duct and an HVAC appliance;

a source of electrical power for the germicidal lamp;

a switch that turns off power to the germicidal lamp when the enclosure is not mounted on the at least one element selected from the group consisting of the HVAC duct and the HVAC appliance;

a base;

a power circuitry located within the base; and a lamp assembly mounted in the base, an electrically powered indicator of lamp illumination, wherein the electrically powered indicator of lamp illumination comprises:

at least two pair of oppositely directed diodes; and a light emitting diode wired in parallel to thereto.

17. An apparatus for monitoring the operation of at least one germicidal lamp used for disinfecting an HVAC system, the apparatus comprising a monitoring circuit, the circuit comprising:

two pairs of oppositely directed diodes connected in parallel; and a light emitting diode connected in parallel therewith, the monitoring circuit being wired in series with a power circuit supplying power to the at least one germicidal lamp.

* * * * *